(12) United States Patent
Nilewski et al.

(10) Patent No.: US 9,738,797 B2
(45) Date of Patent: Aug. 22, 2017

(54) USE OF POLYGLYCEROL PARTIAL ESTERS AS DEFOAMERS

(71) Applicant: Evonik Industries AG, Essen (DE)

(72) Inventors: Margitta Nilewski, Essen (DE); Philippe Favresse, Ratingen (DE); André Scharf, Essen (DE); Petra Gehrmann, Bottrop (DE); Thomas Mettin, Wuppertal (DE); Michael Schwan, Leverkusen (DE); Oliver Springer, Wesel (DE); Tobias Wied, Wuppertal (DE)

(73) Assignee: Evonik Deguesse GmbH, Essen (DE)

( * ) Notice: Subject to any disclaimer, the term of this patent is extended or adjusted under 35 U.S.C. 154(b) by 659 days.

(21) Appl. No.: 13/866,526

(22) Filed: Apr. 19, 2013

(65) Prior Publication Data

US 2013/0281552 A1    Oct. 24, 2013

(30) Foreign Application Priority Data

Apr. 20, 2012   (DE) .................. 10 2012 206 574

(51) Int. Cl.
| | |
|---|---|
| *B01D 19/04* | (2006.01) |
| *C09D 7/12* | (2006.01) |
| *C07C 69/34* | (2006.01) |
| *C08G 65/34* | (2006.01) |
| *C07C 69/50* | (2006.01) |
| *C08G 65/48* | (2006.01) |

(52) U.S. Cl.
CPC ....... *C09D 7/1233* (2013.01); *B01D 19/0404* (2013.01); *C07C 69/34* (2013.01); *C07C 69/50* (2013.01); *C08G 65/34* (2013.01); *C08G 65/48* (2013.01); *C09D 7/125* (2013.01); *C08G 2650/54* (2013.01)

(58) Field of Classification Search
CPC ..... B01D 19/0404; C07C 69/50; C07C 69/34; C08G 65/48; C08G 65/34; C08G 2650/54; C09D 7/1233; C09D 7/125
See application file for complete search history.

(56) References Cited

U.S. PATENT DOCUMENTS

| | | |
|---|---|---|
| 4,690,713 A | 9/1987 | Terae et al. |
| 4,976,888 A | 12/1990 | De Clercq et al. |
| 5,346,511 A | 9/1994 | Dimas et al. |
| 5,429,718 A | 7/1995 | Morlino et al. |
| 5,846,454 A | 12/1998 | Koczo et al. |
| 5,914,362 A | 6/1999 | Brecht et al. |
| 6,605,183 B1 | 8/2003 | Rautschek et al. |
| 6,649,721 B1 | 11/2003 | Dyllick-Brenzinger et al. |
| 6,864,292 B1 * | 3/2005 | Dyllick-Brenzinger ........ B01D 19/0404 162/158 |
| 8,653,289 B2 * | 2/2014 | Wenk ..................... A61K 8/365 424/59 |
| 8,664,175 B2 * | 3/2014 | Wenk ..................... C07C 39/34 510/477 |
| 9,427,385 B2 * | 8/2016 | Meyer .................... A61Q 17/04 |
| 2006/0111453 A1 * | 5/2006 | Bonn .................. B01D 19/0404 516/135 |
| 2008/0069932 A1 * | 3/2008 | Kohori .................... A23D 9/007 426/541 |
| 2010/0212847 A1 * | 8/2010 | Hamers .............. B01D 19/0404 162/75 |
| 2011/0201532 A1 * | 8/2011 | Ponder .................. C11D 3/001 510/220 |
| 2011/0201537 A1 * | 8/2011 | Ponder ................ C11D 3/3707 510/328 |
| 2011/0300082 A1 * | 12/2011 | Wenk ..................... A61K 8/365 424/59 |
| 2012/0308503 A1 * | 12/2012 | Wenk ..................... A61K 8/37 424/70.1 |
| 2012/0309667 A1 * | 12/2012 | Wenk ..................... C07C 39/34 510/515 |

FOREIGN PATENT DOCUMENTS

| | | |
|---|---|---|
| DE | 44 04 202 | 8/1995 |
| DE | 196 41 076 A1 * | 4/1998 |
| DE | 19835968 A1 | 2/2000 |
| EP | 0 403 913 | 12/1990 |
| EP | 0 450 605 | 10/1991 |
| EP | 0 835 862 | 4/1998 |
| EP | 0 878 224 | 11/1998 |
| EP | 2363387 A2 * | 9/2011 |
| WO | WO 00/51708 | 9/2000 |
| WO | WO 2011098310 A1 * | 8/2011 |
| WO | WO 2011098313 A1 * | 8/2011 |
| WO | WO 2011/151114 | 12/2011 |

OTHER PUBLICATIONS

Machine Translation of Publ. No. DE19641076 (A1), published Apr. 1998, European patent Office, obtained online @ http://ep.espacenet.com/?locale=EN_ep (Downloaded Apr. 7, 2016) pp. 1-13.*

* cited by examiner

*Primary Examiner* — Daniel S Metzmaier
(74) *Attorney, Agent, or Firm* — Haug Partners LLP

(57) ABSTRACT

The present invention relates to the use of polyglycerol partial esters as defoamers, in particular in coating and paint applications, to defoamers comprising polyglycerol partial esters, and to corresponding polyglycerol partial esters.

4 Claims, No Drawings

USE OF POLYGLYCEROL PARTIAL ESTERS AS DEFOAMERS

The present application claims priority from German Patent Application No. DE 10 2012 206 574.1 filed on Apr. 20, 2012, the disclosure of which is incorporated herein by reference in its entirety.

FIELD OF INVENTION

The present invention relates to the use of polyglycerol partial esters as defoamers, in particular in coating and paint applications, to defoamers comprising polyglycerol partial esters, and to corresponding polyglycerol partial esters.

It is noted that citation or identification of any document in this application is not an admission that such document is available as prior art to the present invention.

The product class of defoamers has already been used for several decades in many product areas. Examples of these product areas are foods, pharmaceuticals, cosmetics, paper, paints and coatings.

Defoamers bring about the accelerated coalescence of gas bubbles in fluid material systems. As a result of this, the formation of foam is avoided or considerably reduced. If foam fractions are already present prior to adding the defoamers, said fractions are destabilized.

Many known defoamers, as are listed in U.S. Pat. No. 6,605,183, U.S. Pat. No. 5,914,362, U.S. Pat. No. 5,846,454 and U.S. Pat. No. 4,690,713, are based on a combination of silicone oil or silica particles. However, in a large number of material systems, silicone oil or silica particles are to be avoided since other decisive functionalities are destroyed by these components. So-called water-based defoamers, which consist of oil distributed in water (oil in water emulsions), as are described for example by U.S. Pat. No. 4,976,888 and U.S. Pat. No. 5,429,718, have likewise been used since the 1950s in industrial applications.

A further group of defoamers combines ethoxylated polyether having a surface-active structure with polyhydric alcohol fatty acid esters. One example of this is described in U.S. Pat. No. 5,346,511.

The effect of defoamers is determined decisively by their interface-active properties, in particular by the ability to accumulate at the phase interface between different fluid media.

Defoaming substances which are formed as a result of the crosslinking of glycol ether units by means of isocyanates or dicarboxylic acids are described in DE 44 04 202.

Defoaming mixtures of soybean oil, mineral oil, finely divided silicon dioxide, fatty acid monoesters of glycerol and fatty acid monoesters of polyalkoxylated sorbitans are described in EP 0 765 5811.

EP 450605 describes fatty acid-modified diglycerides as part component of a defoamer for foods. WO 00/051708 describes an aqueous defoamer emulsion, the active ingredient of which is based on a polyester modified with fatty acids.

The use of glycerols modified with fatty acid and crosslinked with dicarboxylic acid as emulsifiers is described in DE 25 17 354.

The use of partially esterified (up to 90%) polyglycerols as surfactants is described in JP 2000-230191 A.

EP 0 403 913 A1 describes optionally ethoxylated and/or propoxylated oligoglycerols which are optionally modified with hydroxy-substituted C2- to C18 fatty acids and can be used as pigment dispersants for aqueous coating dispersions.

JP 2011-083715 A describes polyglycerol fatty acid esters as part component of an defoamer composed of a plurality of components.

EP 0 878 224 describes defoaming substances which consist of partially esterified oligoglycerols which have additionally by alkoxylated and are mixed with organic or inorganic solids.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

It is further noted that the invention does not intend to encompass within the scope of the invention any previously disclosed product, process of making the product or method of using the product, which meets the written description and enablement requirements of the USPTO (35 U.S.C. 112, first paragraph) or the EPO (Article 83 of the EPC), such that applicant(s) reserve the right to disclaim, and hereby disclose a disclaimer of, any previously described product, method of making the product, or process of using the product.

SUMMARY OF THE INVENTION

The object of the present invention is to provide improved defoamers which can be adapted to the respective properties of the application coating system present.

DETAILED DESCRIPTION OF EMBODIMENTS

It is to be understood that the figures and descriptions of the present invention have been simplified to illustrate elements that are relevant for a clear understanding of the present invention, while eliminating, for purposes of clarity, many other elements which are conventional in this art. Those of ordinary skill in the art will recognize that other elements are desirable for implementing the present invention. However, because such elements are well known in the art, and because they do not facilitate a better understanding of the present invention, a discussion of such elements is not provided herein.

The present invention will now be described in detail on the basis of exemplary embodiments.

The mode of action of defoamers is dependent on the ability to intervene in interactions at the phase boundary between incorporated air bubbles and the surrounding liquid phase.

In order to be able to intervene in these interactions, an equilibrium between polarity, viscosity and general interface-active properties on the side of the defoamer is necessary.

Often, the establishment of these characteristics for achieving a good defoaming action is simultaneously associated with the negative influence of other coating properties such as e.g. the flow or the general surface quality of the coating film.

The same characteristics of the defoamer which lead to a prevention/reduction in foam burden thus simultaneously also cause an impairment of other important coating properties.

Examples of substances which simultaneously have foam-preventing and coating-surface-impairing properties are the classes of silicone oils and polyether siloxanes.

The problem addressed by the present invention therefore consists in facilitating the prevention/reduction in foam formation in coating systems and at the same time not adversely affecting other coating properties such as e.g. the surface quality.

The stated object is achieved through the use of specifically selected polyglycerol esters as defoamers.

The present invention therefore provides the use of polyglycerol partial esters of saturated or unsaturated, linear or branched fatty acids and/or aromatic monocarboxylic acids and polyfunctional carboxylic acids, which are obtainable by esterification of a polyglycerol mixture with saturated or unsaturated, linear or branched fatty acids having 4 to 22 carbon atoms and/or aromatic monocarboxylic acids having 7 to 22 carbon atoms and polyfunctional carboxylic acids having 4 to 54 carbon atoms and/or their anhydrides or esters as defoamers.

The polyglycerol partial esters according to the invention differ from those from the prior art, for example those in JP 2011-083715, in as much as an additional crosslinking is established by means of dicarboxylic acids between the polyglycerol units in order to adapt the polydispersity to the object to be achieved.

Thus, it has surprisingly been found that specific polyglycerols modified with fatty acid and/or aromatic monocarboxylic acids, in which a crosslinking by polyfunctional carboxylic acids, for example dicarboxylic acids or dicarboxylic anhydrides, is present, are particularly well suited as defoamers. As a result of the crosslinking of the polyglycerol oligomers above and beyond the fatty acid modification of the polyglycerols, additional degrees of freedom are obtained during the synthesis of the defoamer molecules. As a result of this, different physical and/or physicochemical parameters of the resulting molecules, for example viscosity and/or polarity, can be influenced more widely than was hitherto the case. Through such an undertaken optimization of e.g. molar mass, viscosity or polarity, it is possible to achieve a particular defoaming effect.

Corresponding polyglycerol partial esters which are used according to the invention as defoamers are known as such to the person skilled in the art, for example from EP 0 835 862. Particularly preferably, the polyglycerol partial esters used and/or in accordance with the invention have a degree of esterification of the polyglycerol between 76 and 100%, preferably between 80 and 100% and very particularly preferably between 91 and 100%. Polyglycerol partial esters of this type are not known from the prior art, for example from EP 0 835 862.

Consequently, the present invention likewise provides polyglycerol partial esters of saturated or unsaturated, linear or branched fatty acids and/or aromatic monocarboxylic acids and polyfunctional carboxylic acids which are obtainable by esterification of a polyglycerol mixture with saturated or unsaturated, linear or branched fatty acids having 4 to 22 carbon atoms and/or aromatic monocarboxylic acids having 7 to 22 carbon atoms and polyfunctional carboxylic acids having 4 to 54 carbon atoms and/or their anhydrides or esters, where the degree of esterification of the polyglycerol is between 76 and 100%, preferably between 80 and 100% and very particularly preferably between 91 and 100%.

The degree of esterification is determined via a volumetric determination of the acid value (AV). The acid value indicates the mass of mg of KOH which is necessary to neutralize the free acids present in 1 g of product. The acid value can be determined by means of the method described here. The method described was drawn up in accordance with DGF C-V 2, Ph.EUR. 2.5.1, ISO 3682, ASTM D 974, DIN EN ISO 2114.

To determine the acid value, the sample is dissolved in a suitable solvent and then the free acids present are titrated with potassium hydroxide solution.

The solvent used is a mixture of ethanol and toluene in the ratio 1:1. Other possible solvents are e.g. ethanol or isopropanol, where the alternative solvents have no influence on the result of the measurement method. The solvents or solvent mixtures used should only be neutralized in the forefield against phenolphthalein in order to avoid a falsification of the analytical result.

Suitable titrants are inter alia 0.5 N potassium hydroxide solution, 0.1 N potassium hydroxide solution and 0.02 N potassium hydroxide solution. Suitable solvents for the potassium hydroxide solution are water or ethanol.

The indicator used for reaching the transition point can be e.g. a 1% strength phenolphthalein solution in ethanol.

For the actual implementation, the sample to be examined is weighed precisely to 0.1%. Then, ca. 50-100 ml of the neutralized solvent are added and the sample, if necessary, is dissolved with gentle heating.

After adding the phenolphthalein solution, titration is carried out with adjusted potassium hydroxide solution until a constant colour change is reached. For the evaluation, the following calculation formula is used:

$$\text{Acid value [mg } KOH/\text{g]} = \frac{V \times M_{KOH} \times N}{E}$$

Legend:
V=Consumption of titrant [ml]
N=Normality of titrant
E=Initial weight of sample [g]
$M_{KOH}$=Molar mass of KOH Here, the following relationship applies: the degree of esterification increases with decreasing acid value. Taking into consideration the quantitative amount of molecules carrying carboxyl groups used and the quantitative amount of molecules carrying hydroxyl groups used, the degree of esterification can be deduced by means of the acid value.

The acid value stands for the remaining carboxyl groups in the product, and thus permits a conclusion as to the percentage fraction of fully reacted carboxyl groups in the original reactants.

Since, in the course of the esterification step, one hydroxyl group also reacts for each reacting carboxyl group, the number of fully reacted hydroxyl groups is identical to the number of fully reacted carboxyl groups. The percentage fraction of fully reacted hydroxyl groups in the original reactants can ultimately be equated to the degree of esterification.

The polyglycerol partial esters according to the invention or used according to the invention are obtained by esterification and crosslinking of at least three components.

The basis for the polyglycerol partial esters is the polyglycerol mixtures used which are based in particular on polyglycerols having an average degree of condensation of ≥2, i.e. with at least two repeat units, preferably with 2-20 repeat units, particularly preferably with 3-5 repeat units. These are technical-grade polyglycerol mixtures which are obtained e.g. by alkali-catalyzed condensation of glycerol at elevated temperatures, from which fractions with the desired degree of condensation can optionally be obtained by distillation processes. Likewise of suitability are also polyglycerols which are obtained in a different way, e.g. from epichlorohydrin or glycidol.

Particularly suitable polyglycerols have the following oligomer distribution (preferred ranges are given in brackets):

Glycerol: 0.01% by weight to 20% by weight (3% by weight to 12% by weight),
Diglycerols: 0.01% by weight to 60% by weight (20% by weight to 40% by weight),
Triglycerols: 0.01% by weight to 60% by weight (15% by weight to 35% by weight),
Tetraglycerols: 0.01% by weight to 30% by weight (5% by weight to 20% by weight),
Pentaglycerols: 0.01% by weight to 20% by weight (0.1% by weight to 15% by weight) and
Oligoglycerols: ad 100% by weight, where the stated percentages by weight refer to the total amount of polyglycerol used and this distribution is determined using the GC method as detailed below.

The person skilled in the art is aware that, on account of its polymeric property, polyglycerol is a statistical mixture of different compounds. Polyglycerol can have formed ether bonds between two primary, one primary and one secondary or two secondary positions of the glycerol monomers; cyclic structures with one or more rings are likewise known. For details, see e.g. "*Original synthesis of linear, branched and cyclic oligoslycerol standards*", Cassel et al., Eur. J. Org. Chem. 2001, 875-896.

A suitable GC method for determining the homologue distribution involves the hydrolysis or alcoholysis of the (poly)glycerol partial ester according to the invention, separation of the polyglycerol from the resulting acids and analysis by gas chromatography.

For this purpose, 0.6 g of the (poly)glycerol partial ester according to the invention are boiled under reflux for 30 minutes in 25 ml of an ethanolic 0.5 M KOH solution and the pH is adjusted to pH 2-3 with sulphuric acid. The resulting fatty acids are separated off by extracting three times with one volume of petroleum ether in each case. The combined extracts are concentrated by evaporation to ca. 10 mi.

A 0.5 ml sample is admixed in an autosampler vessel with 0.5 ml of MTBE and 1 ml of tritmethylanilinium hydroxide (0.2 M in methanol) and analyzed with GC. This is carried out in a gas chromatograph which is equipped with a split/splitless injector, a capillary column and a flame ionization detector, under the following conditions:

Injector 290° C., split 30 ml
Injection volume: 1 µl
Column: 30 m*0.32 mm HP1 0.25 µm
Carrier gas: Helium, head pressure 70 kPa
Temperature programme: 80° C.-300° C. at 8° C./min, then conditioning for 20 minutes at 300° C.
Detector: FID at 320° C.
Hydrogen 35 ml/min
Air 240 ml/min
Make up gas 12 ml/min By means of this, the fatty acids are separated as their methyl esters according to their carbon chain length. The relative content of the individual fatty acids can be determined by evaluating the peak areas.

The residue extracted with petroleum ether is adjusted to pH 7 to 8 with barium hydroxide, and the precipitated barium sulphate is separated off by centrifugation.

The supernatant is removed and the residue is extracted three times with 20 ml of ethanol.

The combined supernatents are concentrated at 80° C. and 50 mbar, and the residue is taken up in pyridine. A 0.5 ml sample is admixed in an autosampler vessel with 1 ml of N-methyl-N-trifluoroacetamide and heated for 30 minutes at 80° C.

The polyglycerol is analyzed as its trimethylsilyl derivative with GC, using a gas-liquid chromatograph with an on-column injector and flame ionization detector under the following conditions:

Injector: On-column, oven tray
Injection volume: 0.1 µl
Carrier gas: 3 ml/min hydrogen (constant flow)
Column: SimDist 12 m×0.32 mm×0.1 µm (Varian)
Temperature programme: 65° C.-365° C., 10° C./min; then conditioning for 15 minutes at 365° C.
Detector (FID): 375° C.

Under these conditions, the polyglycerol is separated according to the degree of polymerization; additionally, cyclic isomers can be separated from linear isomers up to a degree of polymerization of five. The peak areas of the individual oligomers are separated from one another by a perpendicular at the lowest point between the peaks. Since the resolution for oligomers which have a degree of polymerization greater than six is low, the peak areas for heptaglycerol and higher oligomers are combined and deemed to be heptaglycerol for calculating the polydispersity index. Moreover, cyclic and linear isomers are combined for calculating the polydispersity index.

The relative content of the individual oligomers/isomers can be determined by evaluating the peak areas.

In an analogous manner, this method can also be used in order to characterize the raw materials used which are used for preparing the esters according to the invention.

Within the context of the present invention, "acids" are always also understood as meaning their derivatives, in particular anhydrides or esters, i.e. instead of the free acids it is also possible to use esters and, if possible, also anhydrides.

Further essential components of the polyglycerol partial esters according to the invention or used according to the invention are the saturated or unsaturated, linear or branched fatty acids having 4 to 22 carbon atoms, in particular having 8 to 22 carbon atoms and theft anhydrides or esters. Of suitability in principle for this purpose are all fatty acids of this type known to the person skilled in the art.

Suitable saturated linear fatty acid components are in particular lauric acid, tridecanoic acid, tryristic acid, palmitic acid, margaric acid, stearic acid, arachic acid and behenic acid, and mixtures thereof. Naturally occurring mixtures are, for example, the coconut fatty acids, which comprise as main constituent lauric acid, as well as saturated $C_{14}$- to $C_{18}$-fatty acids and optionally, in small amounts, saturated $C_{18}$- to $C_{10}$-fatty acids and unsaturated fatty acids, and also tallow fatty acids, which are essentially a mixture of palmitic acid and stearic acid.

Suitable saturated branched fatty acid components are in particular isostearic acid and phytanic acid. A further example of a saturated branched fatty acid component is isovaleric acid.

Suitable unsaturated linear fatty acid components are, for example, monoolefinically unsaturated acids, for example hexadecenoic acids, octadecenoic acids, such as oleic acid (cis-9-octadecenoic acid) or elaidic acid (trans-9-octadecenoic acid), eicosenoic acids and docosenoic acids, such as erucic acid (cis-13-docosenoic acid) or brassidic acid (trans- 13-docosenoic acid), polyunsaturated fatty acids, for example octadecadienoic acids and octadecatrienoic acids, such as linoleic acid and linolenic acid, and mixtures thereof. The liquid fatty acids, oleic acid, ricinoleic acid, erucic acid and isostearic acid which contain 18 to 22 carbon atoms are particularly suitable. On account of one branch or one double bond in the hydrocarbon chain, their solidification points are below 35° C. It is also possible to use fatty acid mixtures, which may also comprise wax-like components, such as hydrogenated ricinoleic acid.

Suitable unsaturated branched fatty acid components are, for example, 8-methyl-trans-6-nonenoic acid (Thiele R et al., J Agric Food Chem 2008, 56, 4219) or 11-methyloctadec-12-enoic acid (Spencer G F et al., Lipids 1979, 14, 72).

The saturated or unsaturated, linear or branched fatty acid having 4 to 22 carbon atoms, in particular 8 to 22 carbon atoms, is particularly preferably selected from isostearic acid, oleic acid and/or linolenic acid.

Suitable aromatic monocarboxylic acids having 7 to 22 carbon atoms are in particular benzoic acid, phenylethanoic acid, 4-decyloxybenzoic acid, and/or 4-octadecyloxybenzoic acid or anhydrides or esters thereof, with benzoic acid being particularly preferred.

Further essential components of the polyglycerol partial esters according to the invention or used according to the invention are the polyfunctional carboxylic acids having 4 to 54 carbon atoms. Within the context of the present invention, the term "polyfunctional carboxylic acids" are to be understood as meaning carboxylic acids which have more than one carboxyl group. In particular, the polyfunctional carboxylic acids are aromatic and/or aliphatic dicarboxylic acids or anhydrides or esters thereof.

The aliphatic dicarboxylic acids used for the esterification should have at least 4 carbon atoms. They can be linear or branched, such as e.g. malonic acid, succinic acid, fumaric acid, dimethylglutaric acid or trimethyladipic acid, and anhydrides or esters thereof.

Examples of suitable aromatic dicarboxylic acids are phthalic acid, terephthalic acid, and also isophthalic acid and/or anhydrides thereof. Furthermore, hexahydro-4-methylphthalic anhydride is suitable.

Polyfunctional carboxylic acids, in particular dicarboxylic acids, which can be used are also so-called ditner fatty acids. As is known, these are a mixture of acyclic and cyclic dicarboxylic acids which are obtained by a catalyzed dimerization of unsaturated fatty acids having 8 to 22 carbon atoms. As regards the preparation and use of dimer acids and their physical and chemical properties, reference is made to the publication "The Dimer Acids: The chemical and physical properties, reactions and applications", Ed. E. C. Leonard; Humko Sheffield Chemical, 1975, Memphis, Tenn.

The aforementioned dicarboxylic acids can also contain tri- and polyfunctional carboxylic acids to a lesser extent. The functionality of the mixture should preferably not exceed a value of 2.4 in the molar average.

Polyfunctional carboxylic acids preferred according to the invention are dimer fatty acids, di- and tricarboxylic acids, in particular oxalic acid, fumaric acid, malonic acid, succinic acid, glutaric acid, adipic acid, pimelic acid, suberic acid, azelaic acid, sebacic acid, dodecanedioic acid and/or anhydrides or esters thereof, with dodecanedioic acid, suberic acid and sebacic acid and/or anhydrides or esters thereof being particularly preferred.

The polyglycerol partial esters according to the invention or used according to the invention have in particular a polydispersity of at least 2, preferably of at least 5 and particularly preferably of 3.5 to 5. The preferred polydispersity indicates a branched or hyperbranched polymer structure. This branched or hyperbranched polymer structure contributes to the desired properties of the polyglycerol esters according to the invention or used according to the invention.

Within the context of the present invention, the molar mass distribution and thus the polydispersity is determined in accordance with standard DIN 55672-1. This standard describes the method and the test conditions for ascertaining the molar mass distribution and the molar mass average values $M_n$ (number average) and $M_w$ (weight average) of tetrahydrofuran (THF)-soluble polymers by gel permeation chromatography (GPC). The method described is not an absolute method. Rather, a calibration is necessary, which is carried out using commercially available polystyrene standards that have a linear structure and have been characterized by independent absolute methods.

Within the context of the present invention, the polyglycerol partial esters according to the invention were characterized as follows:

Instrument: Agilent 1100 from Agilent Technologic
Column combination: SDV 1000/10000 Å, length 65.00 cm, temperature 30° C., THF as mobile phase, flow rate 1 ml/min, sample concentration 10 g/l. RI detector, evaluation against polystyrene standard of 162-2520000 g/mol.

The polyglycerol partial esters according to the invention or used according to the invention also preferably have an OH value of 10-160 mg/KOH, in particular 13-14 mg/KOH.

Within the context of the present invention, the hydroxyl value is determined in accordance with DGF C-V 17 a (53), Ph. Eur. 2.5.3. Method A.

Here, the hydroxyl value indicates how many mg of potassium hydroxide are equivalent to the acetic acid bonded by 1 g of the investigated substance during the acetylation.

For the determination, the sample is acetylated with acetic anhydride in the presence of pyridine. One mole of hydroxyl group produces one mole of acetic acid while the excess acetic anhydride produces two moles of acetic acid per mole of acetic anhydride.

The consumption of acetic acid is ascertained or calculated by means of titration from the difference between the main value and a blank value to be carried out in parallel.

The following reagents are needed for the determination.
Pyridine, analytical grade (e.g. Baker Art. No. 8073)
Acetic anhydride >95% (e.g. Baker Art. No. 6068)
For the determination, a mixture of the two reagents is prepared. The mixture consists here of 23% acetic anhydride and 77% pyridine. The mixture is prepared in a tinted glass bottle. The solution is stirred for 24 h prior to use.
Phenolphthalein solution (e.g. Merck Art. No. 7233.0100), 1% strength in ethanol
Potassium hydroxide solution 0.5 mol/l in ethanol Ethanol techn. >98%

Ethanol tech. >98%; neutralized against phenolphthalein using ethanolic potassium hydroxide solution (0.5 mol/l)

dist. water

To achieve an acceptable analytical accuracy, the initial sample weight and the amount of acetylation mixture used are to be chosen such that 4 mols of acetic anhydride are formed per mol of hydroxyl groups. In a 250 ml round flask, the sample amount corresponding to the presumed hydroxyl value is weighed in accurately to +/−0.1 mg on an analytical balance.

The size of the initial weight and the required volume of the acetylation mixture, which is to be added in an accurately metered amount, can be seen from the table below.

| Expected OHV | Acetylation mixture in ml | Initial weight in g |
|---|---|---|
| 10-100 | 5 | 2.00 |
| 100-150 | 5 | 1.50 |
| 150-200 | 5 | 1.00 |
| 200-250 | 5 | 0.75 |
| 250-300 | 5 or | 0.60 |
|  | 10 | 1.20 |
| 300-350 | 10 | 1.00 |
| up to 700 | 15 | 0.75 |
| up to 950 | 15 | 0.50 |
| up to 1500 | 15 | 0.30 |
| up to 2000 | 15 | 0.20 |

Under reflux boiling, the flask filled with sample material and solvent is heated to 95-100° C. After heat treatment for 60 min, 1 ml of dist. water is added. After a further 10 min, the flask is removed from the heat-treatment bath and cooled to room temperature with the help of a water bath.

Liquid condensed at the neck of the flask is transferred to the flask using 5 ml of neutralized alcohol. Then, the titration with 0.5 n potassium hydroxide solution can take place.

The blank experiment likewise required for the calculation is carried out separately in accordance with the above description apart from the addition of sample.

The determination of the acid value of the investigated sample is likewise necessary.

The hydroxyl value is calculated taking into consideration the consumed volume 0.5 n potassium hydroxide solution in the main experiment and blank experiment, and also the acid value of the sample and the initial weight.

The hydroxyl value is calculated according to the following equation $$OHV = \frac{(b-a) \cdot 56.16 \text{ g/mol} \cdot N_{KOH}}{I} + AV$$

a=consumed ml of 0.5 n potassium hydroxide solution in the main experiment b=consumed ml of 0.5 n potassium hydroxide solution in the blank experiment I=initial weight in g $N_{KOH}$=normality of the KOH solution The polyglycerol partial esters according to the invention or used according to the invention further preferably have an acid number of 0.5-14 mg KOH/g, in particular of 10-11 mg KOH/g.

The method of determining the acid value used within the context of the present invention has already been described previously in the description of the degree of esterification.

The polyglycerol partial esters according to the invention or used according to the invention can be prepared in a manner known per se by heating the reaction components and separating off the resulting water of reaction by distillation. To increase the rate, acidic or basic catalysts, such as sulphonic acids, phosphoric acid or phosphorous acid, Lewis acids, such as tin salts, alkali metal or alkaline earth metal oxides or hydroxides, alkoxylates or salts can be added. However, the addition of a catalyst is not absolutely necessary. The polyglycerol partial esters are preferably prepared in a single-stage process. For this, the polyglycerol, the saturated or unsaturated, linear or branched fatty acids and/or aromatic monocarboxylic acids and the polyfunctional carboxylic acids are reacted with one another. The continuing reaction can be monitored e.g. via the separated-off water of reaction, by measuring the acid value or by infrared spectroscopy.

The fraction of polyglycerol during the reaction is in particular 14 to 30% by weight, preferably 15 to 18% by weight, based on the total mixture.

The fraction of saturated or unsaturated, linear or branched fatty acids and/or aromatic monocarboxylic acids during the reaction is in particular 35 to 75% by weight, preferably 65 to 72% by weight, based on the total mixture.

The fraction of polyfunctional carboxylic acids during the reaction is in particular 5 to 40% by weight, preferably 8 to 12% by weight, based on the total mixture.

The reaction takes place in particular at temperatures in the range from 200 to 280° C., in particular in the range from 230 to 250° C.

The polyglycerol partial esters described above are already suitable in an advantageous way for use as defoamers, in particular in coating and paint applications.

Consequently, defoamers comprising polyglycerol partial esters of saturated or unsaturated, linear or branched fatty acids and/or aromatic monocarboxylic acids and polyfunctional carboxylic acids, which are obtainable by esterification of a polyglycerol mixture with saturated or unsaturated, linear or branched fatty acids having 4 to 22 carbon atoms and/or aromatic monocarboxylic acids having 7 to 22 carbon atoms and polyfunctional carboxylic acids having 4 to 54 carbon atoms and/or their anhydrides or esters are likewise provided by the present invention.

Moreover, the defoaming property of the polyglycerol partial esters according to the invention or used according to the invention can be further intensified through the combination with polyethers and/or free fatty acids, i.e. in a further preferred embodiment, the defoamers according to the invention additionally comprise one or more polyethers and/or one or more free fatty acids.

Examples of suitable polyethers are molecules prepared using ethylene oxide and/or propylene oxide as starting materials and which are derived from butanol, propylene glycol or allyl alcohol as starting alcohol. If allyl alcohol-started polyethers are used, polyethers whose terminal hydroxy function has been reacted/capped with methanol are also suitable.

Particular preference is given to butanol-started polyethers in whose preparation preferably propylene oxide has been used from the possible epoxides ethylene oxide and propylene oxide.

Suitable free fatty acids are oleic acid, isostearic acid, ricinoleic acid and linoleic acid, with preferably oleic acid and/or isostearic acid being used.

The physical mixtures obtained here consist preferably of 20-80% by weight of the polyglycerol partial ester, 20-80% by weight of a polyether, and optionally of 2-15% by weight of one or more free fatty acids.

An advantageous defoaming effect can be observed in various coating and paint applications. For example, the advantageous defoaming effect can be ascertained in coating systems based on acrylate oligomers.

In particular, mention may be made of coating systems based on polyester acrylate, urethane acrylate and epoxy acrylate oligomers and also amino-modified oligoether acrylates, which are used in radiation-curing applications.

As a result of the low drying times of only a few seconds customary for the application of these systems, a suitable defoamer must exhibit a very rapid reduction in the foam that arises during processing.

At the same time, only a few surface defects must arise as a result of the defoamer used.

Even without further explanations, it is assumed that a person skilled in the art can utilize the above description in the widest scope. The preferred embodiments and examples are therefore merely to be considered as being a descriptive, but in no way limiting disclosure.

The present invention is described in more detail below by reference to examples. Alternative embodiments of the present invention are obtainable analogously.

EXAMPLES

The parameters specified in the examples are determined in accordance with the methods specified in the description of the invention.

Example 1

Reaction product of polyglycerol (3), isostearic acid and sebacic acid in the stoichiometric ratio 1 mol to 3.5 mol to 0.75 mol.

The starting materials were initially introduced in the stoichiometric ratio polyglycerol (3) 1 mol to isostearic acid 3.5 mol to sebacic acid 0.75 mol in a reaction apparatus and heated to 240° C. with stirring. This temperature was held with stirring until an acid value of <12 mg KOH/g was reached.

The reaction mixture was then cooled with stirring and drawn off.

Ascertained Analytical Characteristic Data:

Degree of esterification according to acid value: 94.5%

OH value: 14 mg/g

Acid value: 11.0 mg/g

Mw: 10814 g/mol

Mn: 2769 g/mol

Polydispersity: 3.9

Examples 2-6

Examples 2-6 were also prepared in the manner described in Example 1.

|  | Example No. | | | | |
| --- | --- | --- | --- | --- | --- |
|  | 2 | 3 | 4 | 5 | 6 |
| Raw material amounts (mol) | | | | | |
| Polyglycerol-3 | 1 mol | 1 mol | 1 mol | 1 mol | 1 mol |
| Isostearic acid | 1.5 mol | 3.25 mol | 3.25 mol | 3.5 mol | 1.5 mol |
| Dimer acid (CAS number 61788-89-4) | 0.75 mol | 0.375 mol | — | 0.75 mol | — |
| Sebacic acid | — | — | 0.375 mol | — | 0.75 mol |
| Characteristic data | | | | | |
| AV [mg KOH/g] | 2.5 | 3.1 | 3 | 5.4 | 0.9 |
| Conversion according to AV in % based on the carboxyl functionalities used | 98.4 | 98.1 | 98.3 | 96.7 | 99.6 |
| Polydispersity (Mw/Mn) | 11.8 | 2.02 | 1.79 | 5.5 | 9.46 |
| Mw [g/mol] | 44335 | 4964 | 3757 | 23431 | 26525 |
| Mn [g/mol] | 3756 | 2467 | 2099 | 4266 | 2804 |
| OH value [mg KOH/g] | 111.0 | 46 | 47 | 11.0 | 145 |

Application-Related Results Found by Way of Example with Respect to the Listed Examples:

To determine the application-related properties, air was stirred into 50 g of an acrylate oligomer mixture (e.g. consisting of aliphatic urethane triacrylates (Ebecryl 265), polyester acrylates (Ebecryl 452) or epoxy acrylates (Laromer 8986) by means of a standard commercial laboratory dissolver (1 min/3000 rpm). In the case of the examples according to the invention, 0.50 g of the polyglycerol partial esters according to the invention were added to the acrylate oligomer mixture.

The foam height after loading stands for the foam height produced when stirring in air.

The time until free from foam stands for the period of time until the resulting foam has completely collapsed.

The assessment of compatibility stands for the influencing of the surface quality. This was assessed on a 10-point scale. 10 corresponds here to no influence at all, and 1 to a very considerable negative influence.

|  | Zero sample without the addition of defoamer | Example No. | | | | | |
|---|---|---|---|---|---|---|---|
|  |  | Example 1 | Example 2 | Example 3 | Example 4 | Example 5 | Example 6 |
| Foam height after loading [mm] | 4 | 1 | 2 | 1 | 1 | 2 | 2 |
| Time until free from foam [min] | 80 | 55 | 60 | 62 | 60 | 55 | 60 |
| Compatibility | 10 | 8 | 7 | 7 | 8 | 8 | 7 |

The application-related examples show that through the use according to the invention of the polyglycerol partial esters as defoamers it is possible to considerably reduce the foam height and the time until free from foam compared with systems without defoamer, without severely impairing the compatibility.

While this invention has been described in conjunction with the specific embodiments outlined above, it is evident that many alternatives, modifications, and variations will be apparent to those skilled in the art. Accordingly, the preferred embodiments of the invention as set forth above are intended to be illustrative, not limiting. Various changes may be made without departing from the spirit and scope of the inventions as defined in the following claims.

The invention claimed is:

1. A method of defoaming a liquid, comprising:
   providing polyglycerol partial esters that are obtained by esterification of a polyglycerol mixture with acids comprising:
   a saturated or unsaturated, linear or branched fatty acid having 4 to 22 carbon atoms, and/or an aromatic monocarboxylic acid having 7 to 22 carbon atoms; and
   a polyfunctional carboxylic acid having 4 to 54 carbon atoms, and/or its anhydride or ester; and
   defoaming the liquid by applying the polyglycerol partial esters to the liquid;
   wherein the degree of esterification of the polyglycerol mixture is between 76 and 100%; and
   wherein the polyglycerol mixture is based on polyglycerols with an average degree of condensation in a range of 3-5.

2. The method according to claim 1;
   wherein acids comprise the saturated or unsaturated, linear or branched fatty acid having 4 to 22 carbon atoms, which is selected from the group consisting of isostearic acid, oleic acid, and linolenic acid.

3. The method according to claim 1;
   wherein the polyfunctional carboxylic acid is selected from the group consisting of oxalic acid, fumaric acid, malonic acid, succinic acid, glutaric acid, adipic acid, pimelic acid, suberic acid, azelaic acid, sebacic acid, dodecanedioic acid, phthalic acid, and their anhydrides and esters.

4. The method according to claim 1;
   wherein the polyglycerol partial esters have a polydispersity of at least 2.

* * * * *